US008881610B2

(12) United States Patent
Wulff et al.

(10) Patent No.: US 8,881,610 B2
(45) Date of Patent: Nov. 11, 2014

(54) WATER SAMPLING DEVICE

(75) Inventors: Thorben Wulff, Mannheim (DE);
Eberhard Sauter, Ritterhude (DE)

(73) Assignee: Alfred-Wegener-Institut Helmholtz-Zentrum fuer Polar- und Meeresforschung, Bremerhaven (DE)

( * ) Notice: Subject to any disclaimer, the term of this patent is extended or adjusted under 35 U.S.C. 154(b) by 315 days.

(21) Appl. No.: 13/379,038

(22) PCT Filed: Jun. 30, 2010

(86) PCT No.: PCT/DE2010/000770
§ 371 (c)(1),
(2), (4) Date: Dec. 19, 2011

(87) PCT Pub. No.: WO2011/000364
PCT Pub. Date: Jan. 6, 2011

(65) Prior Publication Data
US 2012/0096958 A1    Apr. 26, 2012

(30) Foreign Application Priority Data

Jul. 3, 2009   (DE) .......................... 10 2009 032 097

(51) Int. Cl.
*G01N 1/10*      (2006.01)
*G01N 1/12*      (2006.01)
*G01N 1/18*      (2006.01)
*G01N 33/18*    (2006.01)

(52) U.S. Cl.
CPC  *G01N 1/12* (2013.01); *G01N 33/18* (2013.01); *G01N 1/18* (2013.01)
USPC ..................................................... 73/864.63

(58) Field of Classification Search
USPC ................ 73/864.52, 864.63, 864.66, 864.67
See application file for complete search history.

(56) References Cited

U.S. PATENT DOCUMENTS

| 3,489,012 A | 1/1970 | Niskin |
| 4,584,887 A * | 4/1986 | Galen ........................ 73/863.31 |

(Continued)

FOREIGN PATENT DOCUMENTS

| AT | 398002 B | 8/1994 |
| DE | 2221377 A1 | 11/1973 |

(Continued)

OTHER PUBLICATIONS

Waldmann, C., "Compilation of instrument specifications for integration an the ROV of the Ifremer Victor 6000 for the Momareto cruise", Feb 2009, Bremen, Germany, p. 1-21.

(Continued)

*Primary Examiner* — Robert R Raevis
(74) *Attorney, Agent, or Firm* — Leydig, Voit & Mayer, Ltd.

(57) ABSTRACT

A water sampling device includes a mounting frame including two end plates disposed parallel to one another on a shaft. A multiple magazine is configured as a rotatable drum magazine that is horizontally disposed between the two end plates of the mounting frame. The multiple magazine includes a plurality of sample containers. Each of the sample containers has a first face and a second face. The first face includes a first axially arranged conical opening and a first positive locking cone forming an inlet valve. The second face includes a. second axially arranged conical opening and a second positive locking cone forming an outlet valve. Each of the positive locking ,cones is configured to shift axially relative to the respective conical opening so as to operate the respective inlet or outlet valve and so as to form a symmetrical annular gap in an open position of the respective valve.

17 Claims, 5 Drawing Sheets

(56) References Cited

U.S. PATENT DOCUMENTS

| | | | |
|---|---|---|---|
| 4,846,004 A * | 7/1989 | Richards et al. ........... 73/864.63 |
| 4,852,413 A | 8/1989 | Niskin et al. |
| 5,094,113 A | 3/1992 | Wood |
| 5,138,890 A | 8/1992 | Wood |
| 5,303,600 A | 4/1994 | Wood et al. |
| 5,341,693 A | 8/1994 | Banu |
| 5,441,071 A | 8/1995 | Doherty et al. |
| 2004/0173035 A1 | 9/2004 | Britt |
| 2007/0113687 A1 | 5/2007 | Sauter |

FOREIGN PATENT DOCUMENTS

| | | |
|---|---|---|
| DE | 4012625 A1 | 10/1991 |
| DE | 4132410 A1 | 4/1992 |
| DE | 10232623 A1 | 1/2004 |
| EP | 1493656 A1 | 1/2005 |
| GB | 1367276 A | 9/1974 |
| JP | 58044326 A | 3/1983 |
| JP | 1084131 A | 3/1989 |
| JP | 10197419 A | 7/1998 |
| WO | WO 9918421 A1 | 4/1999 |

OTHER PUBLICATIONS

Bird et al, "Development of an active, larger volume, discrete seawater sampler for autonomous underwater vehicles", Monterey Bay Aquarium Res. Inst., Moss Landing, Sep. 2007, p. 1-5.

* cited by examiner

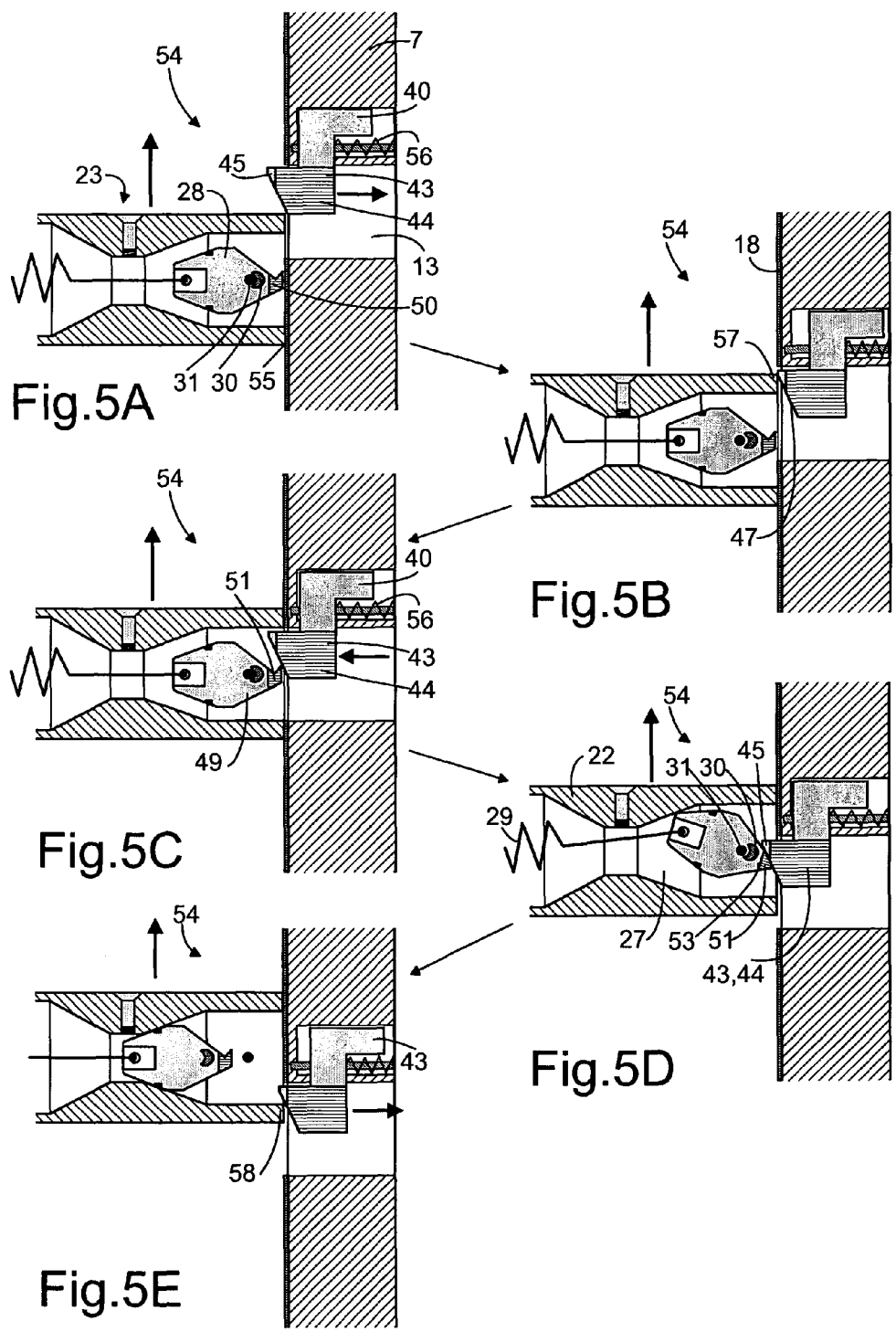

WATER SAMPLING DEVICE

CROSS-REFERENCE TO PRIOR APPLICATIONS

This application is a U.S. National Phase application under 35 U.S.C. §371 of International Application No. PCT/DE2010/000770, filed on Jun. 30, 2010, and claims benefit to German Patent Application No. DE 10 2009 032 097.0, filed on Jul. 3, 2009. The International Application was published in German on Jan. 6, 2011 as WO 2011/000364 under PCT Article 21(2).

FIELD

The invention relates to a water sampling device having several sample containers.

BACKGROUND

JP 58044326 A describes a water sampling device with a plurality of sample containers. A complicated electromechanical mechanism is used to open the sample bottles and then close them again after filled. The sample bottles have only one opening, and they are not flushed. Each bottle exhibits its own complex electromechanical actuation mechanism, which is activated by a motor-driven central cam. JP 01084131 A describes a water sampling device that stores the samples in a shared magazine. A waterwheel held predominantly above the water surface scoops the sample water using cuplike scoops, and guides it into a container, from where it is conveyed into one of the magazine chambers. This device is not suitable for use underneath the surface of the water, and selecting the respective sample container in the magazine is difficult. U.S. Pat. No. 5,441,071 describes a water sampling device having a plurality of sample chambers. Each sample chamber has its own inlet valve. All outputs are interconnected, and a pump acting in both directions conveys the sample water into a storage container in one direction, and a cleaning fluid into the previously used sample chamber in the other direction. The cleaning fluid is flushed out again prior to the next use. The device is conceived for use in contaminated water environments, and having to rinse with cleaning fluid complicates the process and increases the equipment outlay. DE 40 12 625 C2 describes a water sampling device for special use in boreholes, which exhibits no changer, and hence can only take a single sample. An electromechanical mechanism is also used here for opening and closing the single opening to fill the sample container. Sensors acquire specific parameter values of the water, e.g., located in a borehole, and report them to a control unit, which initiates the water sampling process once specific values have been reached. AT 398 002 B describes a water sampling device for use in particular in wells and boreholes, which has no changer, and hence can only take a single sample. The sample container exhibits two valve flaps joined by a string. While the sample container is being lowered into the water, the bottom valve flap is held open by the flow pressure, while the top valve flap is held open by a dwell time magnet. After the desired depth has been reached, gravity moves the bottom valve flap in the sealing direction. The final seal on the sample container is established by pulling on the mooring rope, thereby releasing the upper valve from the dwell time magnet, and moving both valve flaps into the sealed position. The valve mechanism is very simple, and can no longer be used at greater water depths, since it is activated by a pull of the rope. EP 1 493 656 A1 describes a water sampling device that is carried as payload on a submarine. It is provided that a plurality of samples be taken and divided into separate sample containers. A purging device for the inlet conduit is intended to ensure that only the respectively desired water gets into the next sample container. This publication did not describe the kinds of seals and actuation devices in any greater detail. DE 102 32 623 B4 describes a water sampling device that can use a plurality of sample containers horizontally arranged one atop the other in a settling rack to take a profile of groundwater in any body of water desired by simultaneously opening all sample containers and then also simultaneously closing them again after the surrounding water has calmed. The contents in the sample containers represent the layers of water in direct proximity to the floor. The sample containers are sealed on either side with sealing plugs, much like known Niskin bottles. The sealing plugs connected by means of a resilient elastic band are opened when use starts, and held open by an external burn wire. After the water has been sampled simultaneously in all containers, the process of closing the containers is activated when flowing seawater quickly eats through the corrosion wire, so that all sample containers are simultaneously tightly closed by their sealing plugs with the resilient elastic bands. The structural design of this device makes it impossible to use for taking individual water samples per sample container.

The article EXOCET D, WP5, "Compilation of instrument specifications for integration an the ROV of the IFREMER VICTOR 6000 for the MOMARETO cruise", pages 8 and 9, available at ifremer.fr/exocetd/documents/results/5D1.pdf (found on Jun. 5, 2009), describes a "Pepito" water sampling device, which exhibits twenty-five sample containers that can be filled by means of a valve system in the structure housing. A valve controller is not described in the publication. The water sampling device is provided as a load for an independently movable underwater vehicle, and controlled via computer. A flow does not pass through the sample container. The article "Development of an active, larger volume, discrete seawater sampler for autonomous underwater vehicles", available at mbari.org/stall/ryjo/pdfs/Bird_et_al__2007.pdf (found on Jun. 5, 2009) describes a "Gulper" water sampling device, which is used on an AUV (autonomous underwater vehicle), and exhibits ten 2-liter sample containers. Each sample container consists of a cylindrical housing, a one-way inlet valve, and a plunger on the inside, which is pulled up by a tensioned spring at the time the water is being sampled, and draws in the water sample in less than two seconds. The tensioned spring is held in place by a latch. If necessary, a release cord can be pulled, thereby removing the latch and deploying the spring. The rope-pulling activation makes the device unsuitable for use independently of the watercraft at great depths.

DE 41 32 410 A1 describes a sampler with sample containers that can be sealed at the top and bottom by folding covers, similarly to Niskin bottles. The covers are here activated by an outer spring and a trigger mechanism with a rip cord. The sampler avoids the disadvantage of an elastic band running on the interior, which could contaminate the enclosed sample, and thereby falsify a measuring result.

WO 99/18421 A1 describes a sampler that automatically draws in water samples through a filter, subjects the filtrate to biochemical treatment, and can collect the used filter designators in sample tubes after an analysis. The sample tubes are permanently sealed at the bottom, and can be briefly opened at the top by turning a filter carousel just to incorporate another filter designator.

U.S. Pat. No. 7,178,415 B2 describes a sample container similar to a Niskin bottle, in that it exhibits springs arranged on the interior for sealing both ends with folding covers, which are activated by an actuation device. The sample container is convenient, and the covers close tight, so that the samples can remain in the sample container until an analysis can be performed, and refilling is unnecessary. A sample changer is not provided.

U.S. Pat. No. 5,341,693 A describes a fixed sample container with a flexible second inner container, which can be opened and closed in a previously known manner by means of outside spring elements. The material of the inner container prevents the sample from becoming contaminated by the material of the fixed sample container. Air or water can be filled into the space between the containers to regulate the temperature. When removing the sample from the flexible inner container, contact with air can be minimized.

U.S. Pat. No. 5,303,600 A describes a flexible sample container that is collapsed when emptied, and contains no buoyancy-generating air while being deployed to the stipulated depth. Additional drifting weight is avoided. An outer spring-loaded mechanism can open and close the container via rotatably mounted cylinder valves.

U.S. Pat. No. 5,138,890 A describes a trigger mechanism for sealing sample containers on a multiple sampler, which is rotatably mounted on a central axis in the center of the sampler, and can each seal a respective freely selectable sample container via spring-mounted pins and balls by releasing a tether along with spring elements and covers secured thereto on the selected sample container.

U.S. Pat. No. 3,489,012 A describes a trigger mechanism for sealing sample containers on a multiple sampler, which is rotatably mounted on a central axis in the center of the sampler, and can seal the next sample that is sequentially arranged around the axis via spring-mounted pins by releasing a tether along with spring elements and covers secured thereto.

JP 10 197 419 A describes a sample container that can be inwardly opened via conical valve seats, plungers and valve springs located at their inner ends by applying an outer mechanical force along the central axis, and then closed again when unloaded. The sample container has a flexible element that engages through the outer wall, which equalizes the pressure at different water depths without contaminating the samples.

U.S. Pat. No. 4,852,413 describes a water sampling device with a plurality of sample containers, which are rigidly arranged on the outside of a mounting frame in the form of a drum magazine, referred to in the publication as a rosette, with individual attachment devices, and can be individually removed. Each sample container is equipped with one inlet valve and one outlet valve, wherein the inlet valve can be activated from what is also an individual, highly complex electromechanical actuation device, and the outlet valve is synchronously carried along via a rope drive of the inlet valve. Each trigger mechanism has a tensioned torsion spring, which can open its sample container and then close it again exactly one time. The process of opening and closing the next sample container intended for use in taking a water sample can be initiated by way of a selector device in the form of an electromagnet, which can be triggered by an operator or program. The force of the trigger mechanism is guided to the inlet valve via a plug-in hexagonal drive, thereby enabling the removal of the sample container from the mounting frame. The mounting frame is moved perpendicularly through the water layers while suspended on a carrying rope, and water samples can be taken by individually opening and closing the sample containers. Once a sample container has been filled with a water sample and closed, it can only be reused after the sample has been removed on board, and the torsion spring has been tensioned again. The sample containers have a longitudinally oval cross section, with leveled sides to save on space when arranged in the drum magazine. The inlet and outlet valves are long stretched-out openings on the top and bottom faces of the sample containers, which are opened or closed by watertight, rotatably mounted valve cylinders situated in valve inserts lying underneath them. The valve cylinders are activated by the actuation device via the hexagonal drive. The actuation device is distinguished by an intricate interplay between the tripping magnet having a trigger mechanism comprised of two movably connected shafts with leveled areas for the magnetic plunger and stop surfaces on the one hand, and a spiral extension on the other hand, in connection with a hexagonal drive, a driving pin and the torsion spring. The valves and actuation device are very complicated, and hence expensive, sensitive and maintenance-intensive structures.

SUMMARY

In an embodiment, the present invention provides a water sampling device having a mounting frame including two end plates disposed parallel to one another on a shaft disposed at a central longitudinal axis of the mounting frame. A multiple magazine is configured as a rotatable drum magazine that is horizontally disposed between the two end plates of the mounting frame. The multiple magazine includes a plurality of sample containers. Each of the sample containers has a first face and a second face. The first face includes a first axially arranged conical opening and a first positive locking cone forming an inlet valve. The second face includes a second axially arranged conical opening and a second positive locking cone forming an outlet valve. Each of the positive locking cones is configured to shift axially relative to the respective conical opening so as to operate the respective inlet or outlet valve and so as to form a symmetrical annular gap in an open position of the respective valve. An actuation device is configured to seal the inlet and outlet valves. The actuation device includes a respective catch hook disposed on each of the positive locking cones and a respective tripping lever disposed on each of the end plates of the mounting frame. A plurality of positive plug connections are configured to removably attach the sample containers separately to the multiple magazine. A plurality of non-positive clamping connections are configured to attach the sample containers between the end plates of the mounting frame. A selector device including a motor having a gearbox is disposed between the mounting frame and the multiple magazine and is configured to rotate the multiple magazine so as to position a respective one of the sample containers to take a water sample.

BRIEF DESCRIPTION OF THE DRAWINGS

The present invention will be described in even greater detail below based on the exemplary figures. The invention is not limited to the exemplary embodiments. Other features and advantages of various embodiments of the present invention will become apparent by reading the following detailed description with reference to the attached schematic drawings which illustrate the following:

FIG. 5A-E is a five-setting actuation device, side view.

Figure 1:
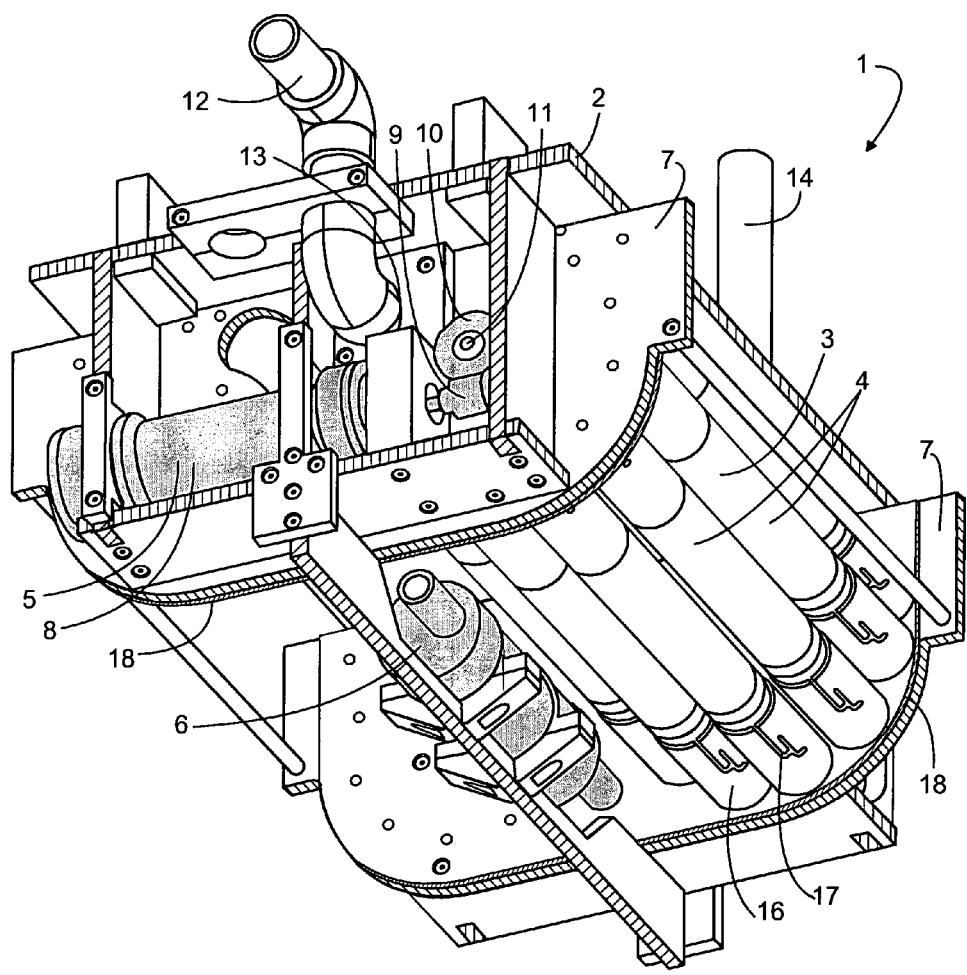
FIG. 1 is a water sampling device according to an embodiment of the invention comprised of a mounting frame fitted with a drum magazine, viewed in perspective from below.

Reference numbers not mentioned or shown on individual Figures and/or in the specification may be gleaned from the other Figures or their description.

DETAILED DESCRIPTION

Water sampling devices make it possible to take very precisely definable water samples from bodies of water of any kind and depth from any type of watercraft, and return them to the surface. The water samples are here individually taken in separate and sealable sample containers, which later can also be individually removed from the water sampling device and sent for analysis. The water sampling process can involve the vertical intake of water profiles, time-lapse water samples from the same location, or any sample sequences desired. For water sampling purposes, the respective sample container is prepared at both faces by opening the inlet and outlet valves. The open sample container is now flushed by moving the entire water sampling device or placing it in a flow existing at the water sampling location. After a freely selectable time has elapsed, the sample container is sealed by sending a trigger signal to the actuation device of the inlet and outlet valves. The desired water sample is now present on the interior in exactly the condition of the water prevailing at the sample location. The next sample location or sample period can then be selected in conjunction with the next sample container. When taking samples at great depths and corresponding water pressures, the differential pressure may cause a very small amount of water to be released through the seals of the inlet and outlet valves while the water sampling device is being returned to the water surface. Since only water is released and none can be taken in, no distortion of the water sample composition takes place.

In an embodiment, the present invention provides a water sampling device having a mounting frame, a multiple magazine with several sample containers, which can be separately removed via individual attachment devices and exhibit an inlet valve on a first face and an outlet valve on a second face, with an actuation device for sealing the inlet and outlet valves, and a selector device for the next sample container to be used for taking a water sample.

In an embodiment, the present invention provides a simplified configuration of the inlet and outlet valves, the actuation device for the inlet and outlet valves, and the selector device for the next sample container intended for use in taking a water sample, significantly improving the construction costs, the weight, the maintenance outlay, and the reliability of the water sampling device.

In the water sampling device according to an embodiment of the invention, a plurality of identical sample containers for taking water samples is arranged in a multiple magazine, here designed as a drum magazine, symmetrically distributed around the periphery. The mounting frame exhibits two end plates arranged parallel to each other, between which the drum magazine is mounted so that it can horizontally rotate around its central axis. The sample containers are joined with the drum magazine by means of positive plug connections, and clamped between the end plates of the mounting frame by means of non-positive clamping connections. Each sample container exhibits an inlet valve on a first face, and an outlet valve on a second face. Water can stream freely through the sample containers with the inlet valves and outlet valves open. After the water samples have been taken, the inlet and outlet valves are closed, and the water sample is securely enclosed on the inside. The inlet and outlet valves are designed as conical openings in the faces of the sample containers, into which locking cones are snugly inserted. The locking cones can be axially shifted, and when shifted into an outer position form symmetrical annular gaps in combination with the accompanying conical opening as their valve seat, i.e., with the inlet and outlet valves opened. When shifted into an inner position, the locking cones establish a positive connection with the accompanying conical opening as their valve seat, i.e., with the inlet and outlet valves closed, hermetically sealing the sample containers. Catch hooks on the locking cones and tripping levers in the faces of the mounting frame comprise the actuation device for closing the inlet and outlet valves of the sample containers. An engine mounted between the mounting frame and drum magazine with a gearbox for turning the drum magazine around its central axis between the faces of the mounting frame comprises the selector device for the next respective sample container to be chosen for taking a water sample.

In an embodiment, the invention provides a cylindrically designed sample containers. The cylindrical shape makes it possible to fabricate the sample containers using a simple, semi-finished product that is available in many materials and diameters, or can be easily manufactured. Because it must be individually manufactured, a cross sectional shape of the sample containers adapted for distribution around a circumference is particularly expensive, and is here avoided.

In an embodiment, the invention provides at least one dowel hole at the cover plates of the drum magazine and at least one dowel pin allocated to each dowel hole on the sample containers as a positive plug connection between the attachment device of the sample container and the drum magazine, and a spring-loaded sleeve slidably mounted on the outlet side of the sample container, with a bayonet lock as the non-positive clamping connection of the attachment device of the sample container between the end plates of the mounting frame. The cover plates of the drum magazine exhibit at least one dowel hole for each sample container, into each of which a dowel pin fixed on the sample containers positively engages. The dowel pins are arranged in one direction, so that the sample containers can be easily accommodated on the drum magazine via simple insertion. In addition, the sample containers are non-positively clamped between the end plates of the mounting frame by having the slidably mounted, spring-loaded sleeve exert the corresponding contact pressure on the outlet side of the sample container. In order to insert a sample container into the drum magazine, the slidable sleeve is pressed against the force of the spring, and its bayonet lock is turned to a locking position. As a result, the sample container is short enough that its pins can be inserted into the cover plates of the drum magazine between the end plates of the mounting frame. After being positively inserted so as to be fixed on the drum magazine, the bayonet lock of the slidable sleeve is moved out of its locking position, the force exerted by the spring pushes away the sleeve, and the sample container is lengthened to a point where it now becomes clamped between the end plates of the mounting frame.

Polyvinyl chloride can advantageously be used as the material for the spring-loaded sleeve. Polyvinyl chloride (PVC) is light, seawater-resistant and—within the range necessary—temperature-resistant, inexpensive, dimensionally stable enough to satisfy the requirements placed on loads arising from the force exerted by the spring, and as opposed to polyethylene, is very easy to process further using known bonding agents. In an embodiment, polytetrafluoroethylene can be used as the coating material for the end plates of the mounting frame, and the inlet side of the sample containers can exhibit a circumferential groove with an inlaid slip ring made out of polytetrafluoroethylene, which protrudes by 0.1 to 2 mm. Clamping the sample containers between the end plates of the mounting frame keeps the frictional force between the faces of the sample containers and end plates of the mounting frame as low as possible while turning the drum magazine by virtue of using polytetrafluoroethylene (PTFE) for the coating of the end plates and the slip ring on the inlet side, and PVC for the sleeve on the outlet side of the sample container.

In addition, the cover plates of the drum magazine can be provided with receptacles in the form of circular segments, which are symmetrically arranged on the periphery at the outer edge for holding the cylindrical sample containers. Such a design supports the positive fixation of the sample containers on the drum magazine.

In an embodiment, catch hooks are provided on the locking cones, with surfaces aligned flush relative to the faces of the sample containers. The flush aligned surfaces comprise impact surfaces for the inflowing sample water, which generate a ram pressure on the inlet side, and a higher internal pressure inside the sample container by comparison to the surrounding water. This prevents unwanted water from penetrating into the sample container while taking a water sample as the result of unavoidable leaks at the clamping site between the end plate of the mounting frame and the face of the sample container on the inlet side. To ensure an authentic water sampling process, collecting water that is unintended for the sample and might be contaminated by impurities is avoided.

In an embodiment, the invention provides for storing the locking cones with concave bearing shells on cylinder pins fixed in the sample containers with the inlet and outlet valves opened, joining the locking cones of the inlet and outlet valves by means of a tension spring running on the inside of the sample containers, as well as fitting springs on the tripping levers in the end plates of the mounting frame, which hold the tripping levers in a first end position at least flush with, but preferably recessed in back of the surfaces of the end plates, and in a second end position protruding at least 1 mm from the end plates. When taking a water sample, the respectively provided sample container with opened inlet and outlet valves sits in front of corresponding openings in the end plates of the mounting frame, through which the sample water is guided. After the water has been successfully sampled, the drum magazine is turned further by the selector device, until the next sample container sits in front of the openings, ready for water sampling. While rotating the sample container filled with the water sample out of the water sampling position, the tripping levers protruding at least 1 mm from the end plates engage into the catch hooks of the locking cones. As turning continues, the locking cones resting with their concave bearing shells on cylinder pins fixed in the sample containers are pulled out of their resting position, during which the bearing is lifted. The tension spring that runs on the interior of the sample container and joins together the locking cones pulls the locking cones into the conical openings in the faces of the sample container and completely seals off the sample container, thereby encapsulating the water sample. Finally, while the drum magazine continues to be rotated, the rear edges of the faces of the filled and sealed sample container will now force the spring-mounted tripping levers back into their position flush relative to the end plates of the mounting frame. As soon as the front edges of the faces of the next sample container have passed the tripping levers, the latter can again assume the position in which they protrude at least 1 mm from the end plates.

In an embodiment, the invention provides for sample containers having a flow vane in the face of the outlet side that can be folded between two end positions. In the position of the sample container prior to water sampling, the flow vane is folded in, held by the closing end plate of the mounting frame, and not visible from outside. After the water has been successfully sampled, the flow vane, which now has a free range of motion before opening the end plate, is folded out by the pressure exerted by the flowing water, and held in this position as the sample container continues to be turned by the once again closing end plate of the mounting frame. It is now visible from outside, documenting that water has been successfully sampled. In the absence of any flow in the sample container during the planned water sampling, the flow vane does not fold out, and remains invisible as turning continues. This documents that water sampling was unsuccessful.

In addition, polyvinylidene fluoride can be advantageously used as the material of the sample container. Polyvinylidene fluoride (PVDF) is completely inert with respect to seawater, and ensures that the encapsulated water sample is chemically unchanged when sent for analysis. Any conduit system that might be used to feed the sample water from outside a watercraft can also be made out of PVDF to reliably prevent contamination. In addition, polyethylene can be advantageously used as a material for the mounting frame. Polyethylene (PE) is light, dimensionally stable, easily to process, and inexpensive, and as a construction material for scientific loads can help significantly in achieving weight reduction.

In an embodiment, the invention provides for the ability to continue incrementally turning the drum magazine by a distance determined by the respective symmetrical arrangement of the sample containers around the periphery each time activated by the selector device. All sample containers are placed in the drum magazine with the inlet and outlet valves in the open position. The actuation device with the tripping levers in the end plates of the mounting frame can only close the sample containers. In the previously described embodiment, each sample container passed by the actuation device is automatically closed. Therefore, the selector device must be controlled in a way that each activation moves the drum magazine incrementally further by a distance defined by the symmetrical arrangement of the sample containers, so that all sample containers are used for sampling water, and are not sealed without a sample. The controller for the selector device is battery powered, and accommodated in a pressure tank on the mounting frame.

FIG. 1 shows a water sampling device 1 according to an embodiment of the invention comprised of a mounting frame 2, here fitted with one of two possible drum magazines 3, viewed in perspective from below. The drum magazine 3 is fitted with cylindrical sample containers 4. The mounting frame 2 further exhibits a selector device 5 for rotating the drum magazine 3, and a controller 6 for controlling the water sampling sequences. The drum magazine 3 is rotatably mounted between two end plates 7 of the mounting frame 2. The selector device 5 turns the drum magazine 3 by means of a motor 8 with a worm 9 and worm wheel 10 on a central shaft 11 of the drum magazine 3. Water is allowed to flow through the sample container 4 provided for taking a water sample by way of a feed line 12 in an inlet opening 13 of the first end plate 7 and a discharge line 14 in an outlet opening 15 (see FIG. 6B) in the second end plate 7 of the mounting frame 2. The sample containers 4 of the drum magazine 3 are clamped between the end plates 7 of the mounting frame 2 by slidably mounted, spring-loaded sleeves 16 with a bayonet lock 17, wherein the end plates 7 exhibit PTFE coatings 18 to reduce friction between the faces of the sample containers 4 and end plates 7 of the mounting frame 2.

Figure 2:
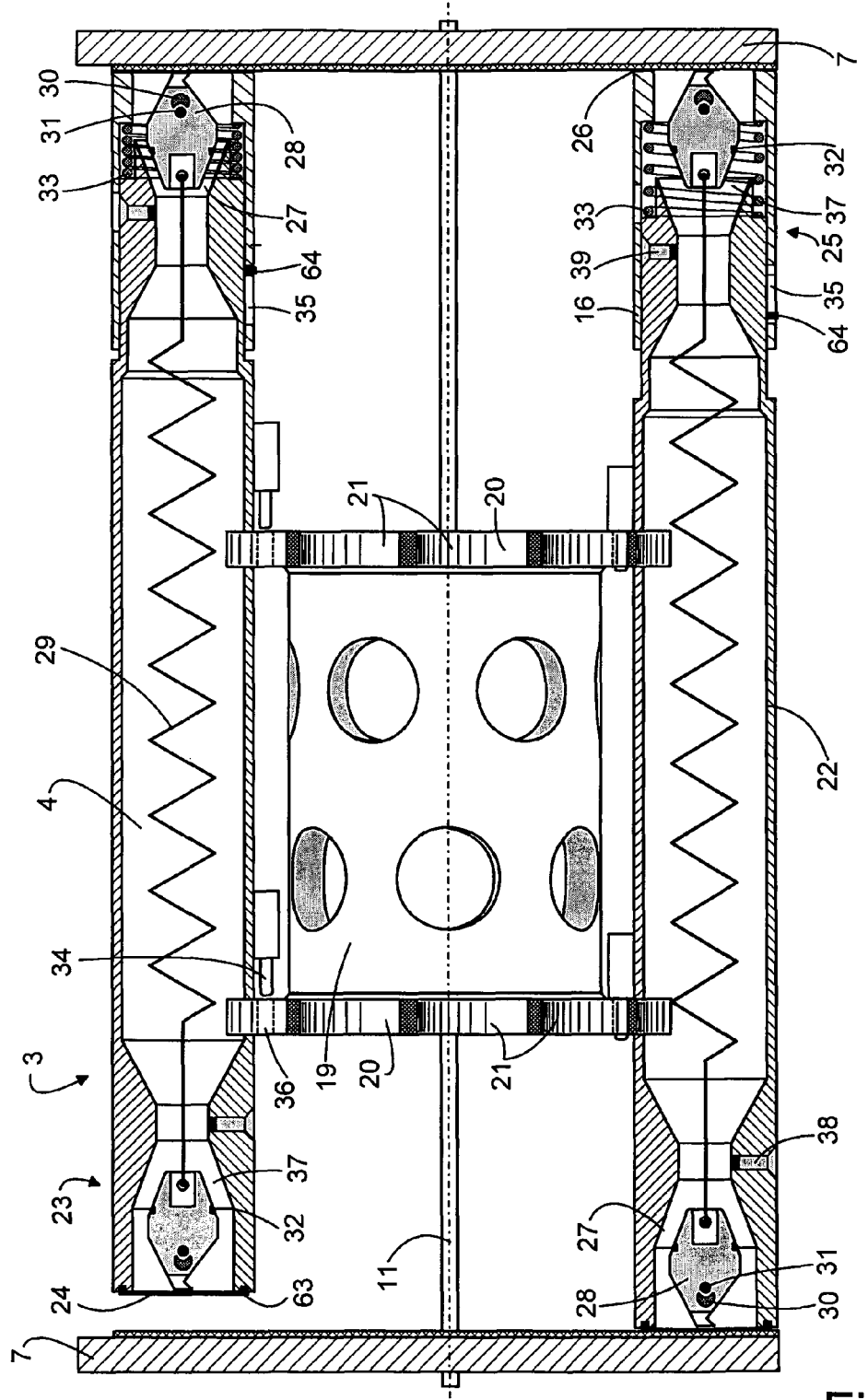
FIG. 2 is a drum magazine with sample containers in various states, side view.

FIG. 2 shows a side view of a drum magazine 3 with sample containers 4 in various states. The drum magazine 3 is rotatably mounted between the end plates 7 of the mounting frame 2 on the central shaft 11, and exhibits a drum body 19 with cover plates 20. The cover plates 20 are provided with receptacles 21 in the form of circular segments symmetrically arranged on the periphery for reliably holding the cylindrical sample containers 4. The sample container 4 at the top is shown prior to being locked in the water sampling device 1, while the sample container 4 at the bottom is shown after being completely locked. Each sample container 4 exhibits a cylindrical sample vessel 22, an inlet valve 23, and a slip ring 63 made of PTFE on its inlet side 24, an outlet valve 25 and a slidably mounted, spring-loaded sleeve 16 on its outlet side 26. The inlet valve 23 and outlet valve 25 are each formed by a conical opening 27 in the sample vessel 22 and a locking cone 28. The locking cones 28 are positively fit in the conical openings 27. Both locking cones 28 are joined by a tension spring 29, and held on cylinder pins 31 fixed in the sample containers 4 via concave bearing shells 30 with the inlet and outlet valves 23, in the open position. O-rings 32 in the locking cones 28 reliably seal them away from the accompanying conical openings 27 with the inlet and outlet valves 23, 25 closed. When pushed together, the slidably mounted sleeves 16 are held against a return spring 33 in a locked position by the bayonet lock 17. To this end, the sleeve 16 is pushed back, and then turned at a right angle thereto, so that a guide pin 64 fixed in the sample vessel 22 in the labyrinth 35 of the bayonet lock 17 is guided in a passageway lying on the periphery of the sleeve 16, and secures the sleeve 16 from being pushed back by the return spring 33. As a safeguard against turning, the sample containers 4 exhibit four cylindrical dowel pins 34, which can be introduced in pairs into accompanying dowel holes 36 of the cover plates 20 of the drum body 19, comprising a positive plug connection. In order to use the sample container 4, the sleeve 16 is moved into the locked position against the force exerted by the return spring 33. The sample container 4 is now placed in one of the receptacles 21 resembling a circular segment in the cover plates 20 of the drum body 19, in such a way that the dowel pins 34 come to lie directly in front of their matching dowel holes 36. The sample container 4 is horizontally shifted to introduce the dowel pins 34 into the dowel holes 36, thereby fixing the sample container 4 in its end position. The sleeve 16 is then turned back, causing the guide pin 74 in the labyrinth 35 of the bayonet lock 17 to be guided into an axially arranged passageway, thereby releasing the sleeve 16. The return spring 33 now axially pushes the sleeve 16 out until it hits the PTFE coating 18 of the accompanying end plate 7 of the mounting frame 2, so as to hold the sample container 4 in a positive clamped connection. After the sample container 4 has been completely placed in the drum magazine 3, the inlet and outlet valves 23, 25 are opened, and form symmetrical annular gaps 37 through which the sample water flows in and out. Finally, the sample containers 4 also each exhibit one discharge opening 38 and one ventilation opening 39, which both are sealed by screws, for draining the collected water sample.

Figure 3:
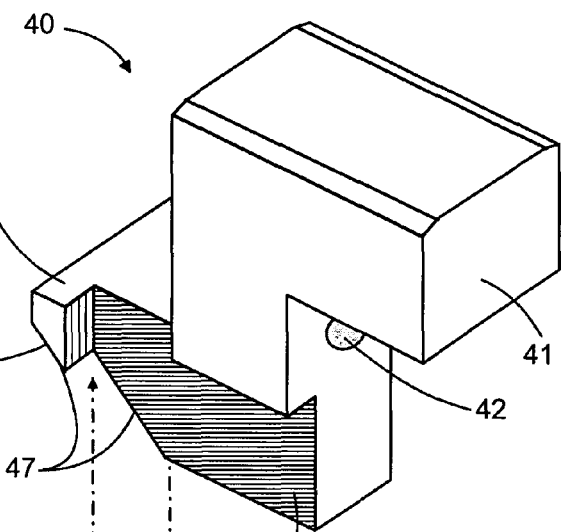
FIG. 3 is a tripping lever, perspective view.

FIG. 3 shows a perspective view of a tripping lever 40. The tripping levers 40 are used to seal the sample containers 4 after the water sample has been taken. They exhibit a guide body 41 with a guide borehole 42 and a catch 43, which is joined as a single piece thereto, projects toward the sample container 4, and consists of a leveled carrier 44 and a nose 45 that symmetrically projects on either side. The leading edge 46 of the catch 43 is designed as an inclined entry 47.

Figure 4:
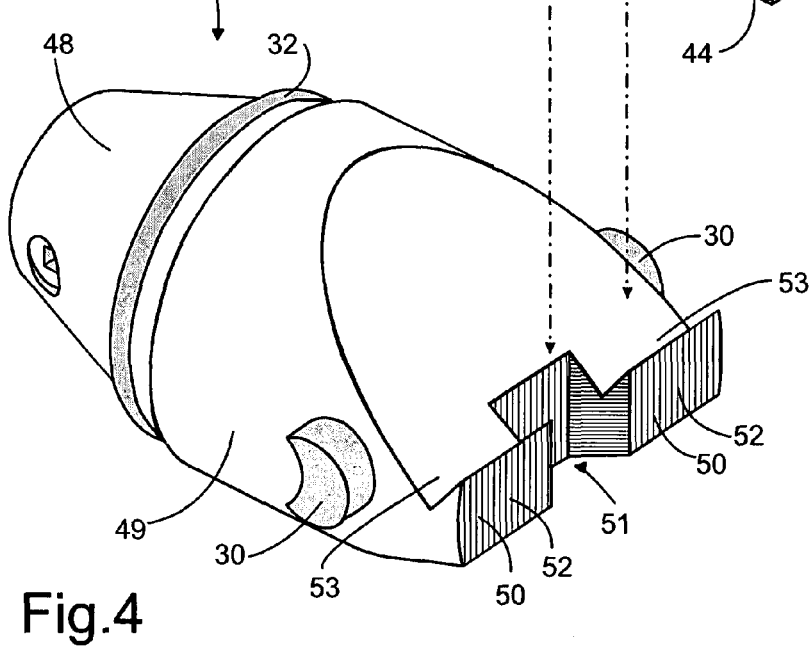
FIG. 4 is a locking cone, perspective view.

FIG. 4 shows a perspective view of a locking cone 28. The locking cones 28 exhibit a conical locking section 48 with the 0-ring 32, and a cylindrical catch section 49. The latter is provided with two catch hooks 50 having a rectangular recess 51 situated in between. The catch hooks 50 each have an impact surface 52 aligned parallel to the face of the sample container 4, and form a back-cut 53 with the remaining catch section 49. The concave bearing shells 30 for mounting the locking cone 28 are arranged on cylinder pins 31 fixed in the sample containers 4 on both sides of the catch section 49.

FIG. 5A-E shows a side view of a five-setting actuation device 54. The actuation device 54 is used to seal the sample container 4 after the water sample has been taken, and is automatically activated by rotating the drum magazine 3 with the selector device 5, here denoted by the perpendicular arrows over the sectionally depicted sample container 4. On FIG. 5A, the face 55 of the sample container 4 starts to cover the inlet opening 13 in the end plate 7 of the mounting frame 2. The locking cone 28 is held with its bearing shells 30 on the cylinder pins 31 with the inlet valve in an open position, and its catch hooks 50 are recessed in back of the face 55 of the sample container 4 by at most 0.5 mm. The tripping lever 40 is located in a first end position determined by a spring 56, wherein the nose 45 and at least 1 mm of the carrier 44 of the catch 43 protrude out of the end plate 7. On FIG. 5B, the leading edge 57 of the face 55 of the sample container 4 has pushed the tripping lever 40 with its inclined entry 47 back into a second end position that is flush relative to the PTFE coating 18 of the end plate 7. On FIG. 5C, the sample container 4 with its opened inlet and outlet valves 23, 25 sits directly in front of the inlet opening 13 of the end plate 7 of the mounting frame 2. At this location, the selector device 5 stops the rotation of the drum magazine 3, and allows the water to be sampled. The tripping lever 40 has here been released from the leading edge 57 of the face 55 of the sample container 4, and returned to its first end position again by the force exerted by the spring 56. The carrier 44 of the catch 43 now sits directly in front of the rectangular recess 51 of the catch section 49 of the locking cone 28. On FIG. 5D, the water sampling process has concluded, and the selector device 5 continues rotating the drum magazine 3 to move the next sample container 4 in front of the inlet opening 13. The carrier 44 of the catch 43 here travels through the rectangular recess 51 in the catch section 49 of the locking cone 28 until the nose 45 of the catch 43 engages the back-cut 53 of the locking cone 28 and takes it along. Because the catch 43 and locking cone 28 are engaged, the catch 43 can no longer be pushed back to its second end position by the locking cone 28 when exposed to the arising forces. The locking cone 28 that was taken along causes it to increasingly tilt until the concave bearing shells 30 slide off the cylinder pins 31 fixed in the sample containers. As soon as the cylinder pins no longer hold the locking cones in the open position of the inlet and outlet valves 23, 25, the joining tension spring 29 pulls the locking cone 28 into its conical openings 27 in the sample vessel 22, thereby reliably sealing the sample container. This state is reached on FIG. 5E. The sample container 4 continues to be turned, and the trailing edge 58 of the face 55 of the sample container 4 now pushes the catch 43 back in the direction of its second end position.

Figure 6A:
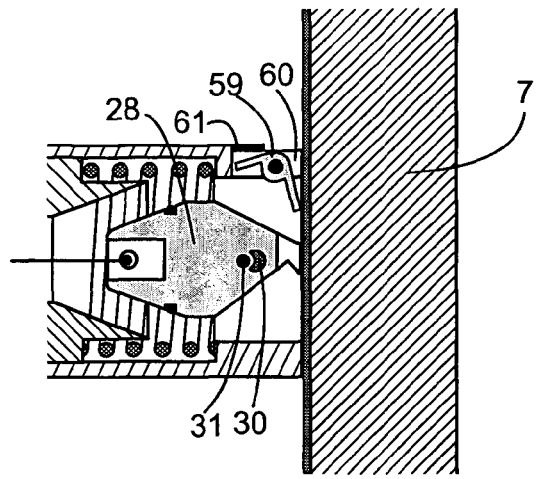
FIG. 6A-C is a three-setting flow vane, side view.
Figure 6B:
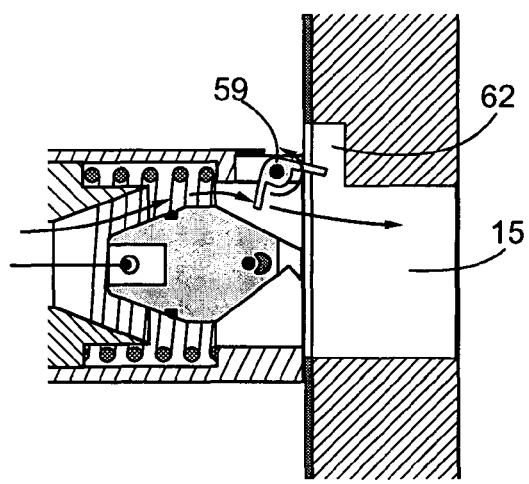
Figure 6C:
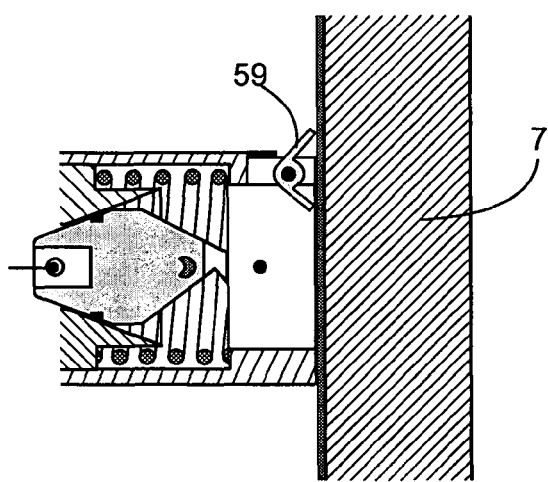

FIG. 6A-C shows a side view of a three-setting flow vane 59. The flow vane 59 serves the purpose of indicating a sample container 4 correctly filled with sample water. In order to take the water sample, the sample containers 4 are placed in the drum magazine 3 with the inlet and outlet valves 23, 25 opened. For this purpose, the locking cone 28 is pulled out of the conical openings 27 against the force exerted by the tension springs 29 that join them together, and held in its position on the cylinder pins fixed in the movable sleeve 16. If the water sampling device 1 is shaken, individual locking cones 28 may unintentionally be removed from their positions, and the accompanying sample container may be sealed. A water sample can then no longer be taken, and the water present in the flooded sample containers 4 does not constitute a correct water sample. The flow vane 59 can only fold over when the sample container 4 is carrying a flow of water and in a position to sample water in front of the outlet opening 15 of the end plates 7 of the mounting frame 2. If the flow vane 59 is found not to be folded over while removing the sample container 4, the sample container 4 does not contain a correct water sample. The flow vane 59 is rotatably arranged in a recess 60 of the movable sleeve 16 on the outlet side of the sample container 4. A stop 61 limits the rotational motion. FIG. 6A shows the initial setting of the flow vane 59 while placing the sample containers 4 in the drum magazine 3. The flow vane 59 is folded in, and held in this position by the end plate 7 of the mounting frame 2. On FIG. 6B, the sample container 4 is in position for taking a water sample, with its outlet side 26 in front of the opening 27 in the end plate 7 of the mounting frame 2. The opening 27 is provided with additional movement space 62, which allows the flow vane 59 to rotate exclusively into this position. If a flow passes through the sample container 4 (here denoted by three arrows), the flow vane 59 is folded out by the water pressure, and limited in its motion by the stop 61. On FIG. 6C, the drum magazine was rotated further. The sample container 4 again sits in front of a closed section of the end plate 7, thereby fixing the flow vane 59 in its outwardly rotated position, and signaling that the water sample was successfully taken.

While the invention has been described with reference to particular embodiments thereof, it will be understood by those having ordinary skill the art that various changes may be made therein without departing from the scope and spirit of the invention. Further, the present invention is not limited to the embodiments described herein; reference should be had to the appended claims.

The invention claimed is:

1. A water sampling device comprising:
a mounting frame including two end plates disposed parallel to one another on a shaft disposed at a central longitudinal axis of the mounting frame, each of the end plates including a tripping lever;
a multiple magazine configured as a rotatable drum magazine that is horizontally disposed between the two end plates of the mounting frame, the multiple magazine including a plurality of sample containers, each of the sample containers having a first face and a second face, the first face including a first axially arranged conical opening and a first locking cone forming an inlet valve, the second face including a second axially arranged conical opening and a second locking cone forming an outlet valve, each of the locking cones having a catch hook configured to engage with a respective one of the tripping levers to seal the inlet and outlet valves, the locking cones being configured to shift axially relative to the respective conical opening so as to operate the respective inlet or outlet valve and so as to form a symmetrical annular gap in an open position of the respective valve;
a plurality of plug connections configured to removably attach the sample containers separately to the multiple magazine;
a plurality of clamping connections of the sample containers configured to attach the sample containers between the end plates of the mounting frame; and
a selector device configured to rotate the multiple magazine so as to position a respective one of the sample containers to take a water sample.

2. The water sampling device according to claim 1, wherein the sample containers are cylindrical.

3. The water sampling device according to claim 2, wherein the multiple magazine includes cover plates having receptacles configured as circular segments symmetrically disposed about an outer edge of the multiple magazine so as to hold the cylindrical sample containers.

4. The water sampling device according to claim 1, wherein the multiple magazine includes at least one cover plate and the plug connections include at least one dowel hole disposed in each of the at least cover plate and at least one dowel pin disposed on a respective one of the sample containers and corresponding to a respective one of the at least one dowel hole.

5. The water sampling device according to claim 1, wherein the clamping connections include a spring-loaded sleeve slidably disposed on an outlet side of each of the sample containers having a bayonet lock.

6. The water sampling device according to claim 5, wherein the spring-loaded sleeve includes polyvinylchloride.

7. The water sampling device according to claim 1, wherein the end plates of the mounting frame include a coating of polytetrafluoroethylene.

8. The water sampling device according to claim 1, wherein each of the sample containers include a circumferential groove having an inlaid slip ring which includes polytetrafluoroethylene and protrudes by 0.1 to 2 mm.

9. The water sampling device according to claim 1, wherein each catch hook includes a surface aligned flush relative to a respective one of the faces of the sample containers.

10. The water sampling device according to claim 1, wherein each of the tripping levers includes a spring configured to hold the tripping lever in a first end position flush with or recessed behind a surface of the respective one of the end plates and in a second end position protruding at least 1 mm from the surface of the respective one of the end plates.

11. The water sampling device according to claim 10, wherein each spring is configured to hold the tripping lever in the first end position recessed behind the surface of the end plate.

12. The water sampling device according to claim 1, wherein each of the sample containers includes a flow vane that is foldable between two end positions in a spring-loaded sleeve disposed on an outlet side of each of the sample containers.

13. The water sampling device according to claim 1, wherein the sample containers include polyvinylidene fluoride.

14. The water sampling device according to claim 1, wherein the mounting frame includes polyethylene.

15. The water sampling device according to claim 1, wherein the respective locking cones of each sample container are joined by a tension spring disposed in an interior of the sample container.

16. The water sampling device according to claim 1, wherein the respective locking cones of each sample container include a concave bearing shell that is disposed, in the open position of the respective valve, on a cylinder pin that is fixed in the sample container.

17. The water sampling device according to claim 1, wherein the selector device is configured, each time the selector device is activated, to incrementally rotate the multiple magazine by a distance that is based on a respective symmetrical arrangement of the sample containers around a periphery of the multiple magazine.

* * * * *